United States Patent [19]

DiPippo

[11] Patent Number: 5,009,890

[45] Date of Patent: Apr. 23, 1991

[54] BURN TREATMENT PRODUCT

[75] Inventor: Ascanio G. DiPippo, Middletown, R.I.

[73] Assignee: Trilling Medical Technologies, Inc., Carlstadt, N.J.

[21] Appl. No.: 512,621

[22] Filed: Apr. 11, 1990

Related U.S. Application Data

[63] Continuation of Ser. No. 83,395, Aug. 10, 1987, abandoned, which is a continuation-in-part of Ser. No. 32,268, Mar. 31, 1987, abandoned.

[51] Int. Cl.$^5$ .................. A61K 35/78; A61L 15/44
[52] U.S. Cl. ................... 424/195.1; 169/50; 128/155
[58] Field of Search ..................... 424/195.1

[56] References Cited

U.S. PATENT DOCUMENTS 3,902,559  9/1975  Everingham et al. ............. 169/50
4,784,842  11/1988  London et al. .................. 424/195.1

OTHER PUBLICATIONS

Hawley, The Condensed Chemical Dictionary, 10th edition, pp. 566 and 774.

Primary Examiner—Olik Chaudhuri
Assistant Examiner—Ellen M. McAvoy
Attorney, Agent, or Firm—Blum Kaplan

[57] ABSTRACT

A burn treatment product in the form of a therapeutic, non-toxic, bactericidal, water-soluble and bio-degradable gel is provided. The active ingredients of the product are water and Tea Tree Blend. A gum material is used to maintain the water and Tea Tree Blend in a gel state. Other ingredients are also provided for increasing shelf life and for imparting bactericidal properties.

48 Claims, No Drawings

BURN TREATMENT PRODUCT

CROSS-REFERENCE TO RELATED APPLICATIONS

This is a continuation of application Ser. No. 83,395, Aug. 10, 1987, abandoned, and a continuation-in-part of copending U.S. patent application Ser. No. 07/032,268, filed Mar. 31, 1987, now abandoned.

BACKGROUND OF THE INVENTION

This invention relates to burn treatment products and, in particular, to a burn treatment product that is useful for decreasing the temperature at the surface of a burn wound so as to lessen the extent of injury to a burn victim.

Numerous fire extinguishers or burn treatment products and devices are available. Of these, many of the fire extinguishers make use of asbestos cloth. Exemplary of such devices are those disclosed in U.S. Pat. No. 360,998 issued to J. W. Cloud on April 12, 1887 and British Patent Specification No. 340,172 accepted on Dec. 24, 1930. However, it is now known that asbestos is an extremely carcinogenic material and its use has fallen into disfavor throughout the world.

Medicated pads and bandages for treatment of wounds, including burn wounds, are also well known. Exemplary pads and bandages are disclosed in U.S. Pat. Nos. 3,062,210; 3,089,492; 3,395,063; 3,624,224; 3,657,760; and 3,750,666.

In addition, U.S. Pat. No. 3,902,559 issued to Everingham et al on Sept. 2, 1975 discloses a fire fighting appliance. The fire fighting appliance includes a blanket-like carrier soaked in a viscous aqueous solution of a thickening agent. The fire fighting appliances disclosed are manually applied to a fire or to a burn victim.

The carrier is preferably a 100% pure new wool carrier having a specified yarn count, fabric structure and strength. The thickening agent solution contains a bactericide. One preferred bactericide is tea tree oil.

As disclosed in the patent, tea tree oil is a natural oil obtained from Melaleuca alternifolia, a tree that grows on the north coastal areas of the state of New South Wales and in southern Queensland, Australia. The principle active constituents of tea tree oil are 1-terpinen-4-ol, terpinolene, cineole, sesquiterpenes, p-cymene and pinene. Similar types of oils are obtained from allied species of Melaleuca such as Melaleuca lineariifolia and Melaleuca leucadendron.

Firefighting appliances and burn treatment products manufactured in accordance with this patent are currently on the market in the United States and throughout the world. Such appliances have been found to be useful not only for fighting fires but also for treatment and debridement of burns.

With respect to the treatment of burns, the main objectives are to relieve pain, prevent contamination and eliminate the source of heat. Dry dressings do not eliminate the heat source. In fact, dry dressings retain heat and cause the burn area to enlarge, thereby intensifying the severity of the injury. In addition, dry dressings provide little protection against contamination and pain and usually adhere to burnt clothing and skin tissue. A great deal of pain and skin damage can result from the removal of dry dressings.

Ordinary tap water has also been used in emergency situations, but it is not practical and only superficially eliminates the heat source. Furthermore, water does not rapidly penetrate through clothing or skin tissue. In addition, tap water does not provide protection against contamination and can even cause contamination. Tap water can also irritate exposed nerve endings causing intensified pain and discomfort. Finally, hypothermia can be induced by the use of tap water because water cools by evaporation.

It is, therefore, desirable to provide an improved burn treatment product that has good bactericidal activity and that aids in the healing of burn wounds.

SUMMARY OF THE INVENTION

Generally speaking, in accordance with the invention a burn treatment product is provided. The product is in the form of a therapeutic, non-toxic, bactericidal, water-soluble and bio-degradable gel. The active ingredients of the product are water and Tea Tree Blend sold by G. R. Davis Pty Ltd of Hornsby, Australia. A gum material is used to maintain the water and Tea Tree Blend in a gel state. Other ingredients are also provided for increasing shelf life and for imparting additional bactericidal properties.

It is, therefore, an object of the invention to provide an improved burn treatment product.

It is a further object of the invention to provide a burn treatment product prepared using Tea Tree Blend.

It is another object of the invention to provide a burn treatment product that can be applied directly to a burn wound in gel form.

It is still another object of the invention to provide a burn treatment product that can be applied directly to a burn injury in the form of a carrier impregnated with a gel.

It is a still further object of the invention to provide a burn treatment product that is therapeutic, non-toxic, bactericidal, water-soluble and bio-degradable.

Still other objects and advantages of the invention will in part be obvious and will in part be apparent from the specification.

The invention accordingly comprises a product possessing the features, properties, and the relation of components and the several steps and the relation of one or more of such steps with respect to each of the others thereof, which will be exemplified in the product and method hereinafter described, and the scope of the invention will be indicated in the claims.

DETAILED DESCRIPTION OF THE PREFERRED EMBODIMENTS

The burn treatment product prepared in accordance with the invention is a gel containing water and Tea Tree Blend as its active ingredients. A gum material is used for forming the gel and keeping the Blend evenly dispersed in the aqueous solution. Additional ingredients are used to improve the shelf life and impart bactericidal properties.

In a preferred embodiment, ordinary tap water, purified water, sterile water, halogenated water, especially chlorinated water which is also known as bleach water or chloropactin and mixtures thereof are used. The water is used in an amount between about 80 and 98% by weight of the solution. In a more preferred embodiment, the amount of water is between about 90 and 97% by weight of the solution.

Tea Tree Blend is a mixture of terpenes and terpinols that are generally naturally occurring, but can be synthetically prepared. The terpene and terpinol compounds can be obtained either as pure compounds derived from the natural oils or as mixtures of components derived from plants of *Melaleuca alternifolia, Melaleuca lineariifolia, Melaleuca leucadendron, Eucalyptus longirostris* and closely related species. In a preferred embodiment, Tea Tree Blend is a blend of tea tree oil and certain distillate fractions of eucalyptus oil which provides a product having characteristics similar to those of tea tree oil and which can be used to extend the available supply of tea tree oil. However, it has now been discovered that a burn treatment product prepared in accordance with the invention using Tea Tree Blend has enhanced bactericidal properties as compared with a similar burn treatment product prepared using tea tree oil. Although Tea Tree Blend and tea tree oil are similar in many respects, Tea Tree Blend has a higher proportion of levo-rotary enantiomers. It is thought that it is these levo-rotary enantiomers that lead to the enhanced properties of a burn treatment product prepared using Tea Tree Blend. Tea Tree Blend has the following major constituents in the approximate percentages designated below, as determined by gas chromatography in combination with mass spectrometry. All percentages are by weight and can vary by up to about plus or minus 10%.

| | |
|---|---|
| $\alpha$-p-mentha 1,5,diene | 0–35% |
| $\alpha$-terpineol | 15–20% |
| terpinen-4-ol | 12–15% |
| 1,8,cineole | 7–14% |
| $\alpha$-terpinene | 4% |
| p-cymene | 3–7% |
| $\gamma$-terpinene | 3–7% |
| $\alpha$-pinene | 2–6% |
| limonene | 1–5% |
| aromadendrene | 1% |
| terpinolene | 1–3% |
| myrcene | 0–1% |
| $\alpha$-phellandrene | 0–14% |

The remainder of the Blend is made up of some or all of the following compounds, with no single compound being above about 1% of the Blend.

$\beta$-pinene
camphene
camphor
sabinene
myrcene
1,4,cineole
hexanol
allyl hexanoate
p-$\alpha$-dimethylstyrene
$\alpha$-cubebene
$\alpha$-copaene
$\alpha$-gurjuene
linalool
1-terpineol
$\beta$-terpineol
$\beta$-elemene
caryophyllene
alloaromadendrene
humulene
$\gamma$-muurolene
$\alpha$-muurolene
viridiflorene
piperitone
piperitol
$\alpha$-cadiene
nerol
geraniol
8-p-cymenol
calamenene
4,10-dimethyl-7-isopropyl bicyclo(4,4,0)-1-4-decadiene
$\alpha$-eudesmol
$\beta$-eudesmol
australol
traces of sesquiterpenes Since the Blend is not a natural oil, the variation in composition exhibited by natural oils can be minimized. However, some variation is still present, particularly in the minor constituents.

The physical constants of the Blend are generally as follows:

| | |
|---|---|
| Refractive index at 20° C. | between about 1.4743 and 1.4813 |
| Relative density at 20° C. | between about 0.890 and 0.910 |
| Optical rotation at 20° C. | between about $-14°$ and $-24°$ |
| Solubility in 85% ethanol (v/v) at 20° C. | soluble in less than about 1.5 vols |
| General description | clear, colorless to pale yellow liquid, mobile at 20° C. |

Tea Tree Blend was tested for bactericidal activity against a variety of organisms and the following results were obtained for a 1:125 dilution of the Blend in water, a 1:250 dilution of the Blend in water and a reference standard:

| | 1:125 | 1:250 | Ref. stand |
|---|---|---|---|
| TIME 0 | | | |
| Staphylococcus aureus | $8.2 \times 10^5$ | $1.5 \times 10^6$ | $1.4 \times 10^6$ |
| Escherichia coli | $5.0 \times 10^1$ | $2.1 \times 10^3$ | $9.5 \times 10^5$ |
| Pseudomonas aeruginosa | $<1.0$ | $1.6 \times 10^6$ | $1.5 \times 10^6$ |
| Pseudomonas vulgaris | $6.0 \times 10^1$ | $1.0 \times 10^3$ | $7.4 \times 10^5$ |
| Candida albicans | $5.1 \times 10^4$ | $6.7 \times 10^4$ | $5.8 \times 10^4$ |
| Aspergillus niger | $3.0 \times 10^5$ | $7.5 \times 10^5$ | $7.5 \times 10^5$ |
| TIME 7 DAYS | | | |
| Staphylococcus aureus | $<1.0$ | $<1.0$ | $<1.0$ |
| Escherichia coli | $<1.0$ | $<1.0$ | $1.7 \times 10^6$ |
| Pseudomonas aeruginosa | $<1.0$ | $1.1 \times 10^7$ | $1.4 \times 10^6$ |
| Pseudomonas vulgaris | $<1.0$ | $<1.0$ | $2.8 \times 10^5$ |
| Candida albicans | $<1.0$ | $<1.0$ | $4.9 \times 10^4$ |
| Aspergillus niger | $5.5 \times 10^5$ | $4.5 \times 10^5$ | $4.5 \times 10^5$ |
| TIME 28 DAYS | | | |
| Staphylococcus aureus | $<1.0$ | | $<1.0$ |
| Escherichia coli | $<1.0$ | | $9.1 \times 10^5$ |
| Pseudomonas aeruginosa | $<1.0$ | | $4.6 \times 10^5$ |
| Pseudomonas vulgaris | $<1.0$ | | $7.3 \times 10^5$ |
| Candida albicans | $<1.0$ | | $1.1 \times 10^5$ |
| Aspergillus niger | $5.0 \times 10^4$ | | $4.5 \times 10^5$ |

Apparently it is the interaction of the various compounds in the Tea Tree Blend that provides the germicidal effect. Use of any of the compounds separately is not effective.

The Tea Tree Blend itself is flammable and is used in an amount of less than about 20% of the burn treatment product. In an alternate embodiment of the invention, Tea Tree Blend is used in combination with tea tree oil and the total amount of Tea Tree Blend and tea tree oil is less than about 20%. In a more preferred embodiment, the Tea Tree Blend or Tea Tree Blend and tea tree oil is used in an amount between about 0.1 and 5.0%, more preferably, between about 0.5 and 1.5%.

A gum is used as a thickening agent to provide a gel of increased viscosity. The function of the gum is to keep the water in place and to provide a gel. Any type of gum can be used. Suitable gums include, but are not limited to, xanthan gum, locust bean gum, guar gum and the like and mixtures thereof. In one especially preferred embodiment of the invention, KELGUM ® manufactured by Kelco Company of Clark, New Jersey is used. KELGUM ® is a 50—50 mixture of xanthan gum and locust bean gum. The gum is used in an amount of between about 0.5 and 5% by weight. More preferably, the gum is used in an amount between about 0.5 and 3% by weight and most preferably, the gum is used in the amount of between about 0.6 and 1% by weight.

Alternatively, either KELTROL ® or KELSET ® can be used as all or part of the gum material. Both KELTROL ® and KELSET ® are manufactured by Kelco Company of Clark, New Jersey. KELTROL ® is 100% xanthan gum and KELSET ® is 100% calcium alginate, a gum-type material.

Other ingredients are also optionally included in the burn treatment product prepared in accordance with the invention. One such ingredient that can be used for providing smoothness and emollient properties is glycerin. Glycerin can be used either alone or in solution of sorbitol or other physiologically safe polyhydroxy compounds such as propylene glycol. Glycerin is used in a maximum of up to about 5% by weight and preferably between about 0.5 and 3%. Most preferably, glycerin is used in an amount of about 1%.

Another optional ingredient that can be included is iodine. Iodine provides anti-bacterial effects, particularly against Pseudomonas organisms. The iodine can be provided as a 1% liquid iodine solution. For example, a 10% Povodone iodine solution provides 1% iodine. The iodine can be used in an amount between about 0.01 and 1%, more preferably, between about 0.01 and 0.1%, and most preferably, about 0.02%.

A surfactant or surface active agent can be used in a quantity sufficient to maintain the emulsion. In a preferred embodiment, the amount of surfactant is between about 0.07 and 0.25% by weight, preferably about 0.14%. Suitable surfactants include, but are not limited to, SURFAX 90 ® and octoxynol 9.

Zephyrin chloride or other equivalent compounds can be used as a germicidal agent in addition to a surfactant to replace some of the iodine. Suitable equivalent compounds can include quatenary compounds such as benzalkonium compounds.

A liquid preservative such as PHENONIP ® can also be included. PHENONIP ® is a mixture of phenoxyethanol, methylparaben, ethylparaben, propylparaben and butylparaben. Such a preservative should be used in an amount between about 0.125 and 0.35% by weight, more preferably, between about 0.2 and 0.25% ±0.01%.

Methylparaben is a bacteriostat and can be used as a preservative either with or without PHENONIP ® Such a preservative can be used in an amount between about 0.01 and 0.5%, more preferably about 0.25%.

In still another alternate embodiment, diazolidinyl urea or imidazolidinyl urea II is used as a preservative. Imidazolidinyl ure II is sold under the tradename GERMALL ® II by Sutton Laboratories, Inc. It has the molecular formula $C_8H_{14}N_4O_7$ and the chemical name N-(Hydroxymethyl-N-(1,3-dihydroxymethyl-2,5-diox-o-4-imidazolidinyl-N'-hydroxymethyl) Urea. The structure is:

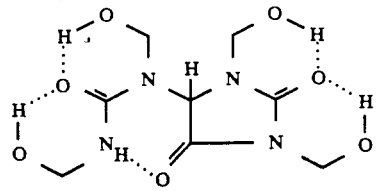

GERMALL ® II is a useful preservative because it has a wide spectrum of activity, particularly against troublesome house microorganisms. It is active against gram negative bacteria such as Pseudomonas as well as against yeast and mold. The urea is preferably used in an amount between 0.1 and 0.35%. It can be used alone or in combination with parabens.

Pre-mixed combinations of ingredients are aso suitable. For example, GERMABEN ® manufactured by Sutton Laboratories, Inc. can be used as a replacement for some or all of the parabens and the iodine.

The following examples show the preparation of burn treatment products prepared in accordance with the invention. These examples are presented for purposes of illustration only and are not intended to be construed in a limiting sense.

EXAMPLE 1

1¼ ounces of 1% liquid iodine was added to 7 ounces of SURFAX 90 ® and mixed thoroughly. The iodine faded into the SURFAX 90 ® and the mixture became thick. 12 ounces of PHENONIP ® was added and mixed thoroughly for about 20 to 30 seconds. The mixture became liquified and smooth and 28 ounces of Tea Tree Blend was added. The resulting mixture was again mixed thoroughly and poured into 4 pounds of glycerin.

Separately, 2¼ pounds of KELGUM ® and 12½ ounces of methylparaben both in powder form were combined and mixed. The liquid mixture and the powder mixture were mixed together and stirred to obtain a liquid mixture. The mixture became creamy smooth. The resulting mixture was poured into 40 gallons of water and mixed for approximately 15 minutes. The burn treatment product obtained had a soft fluid action. It was in the form of a gel and clung to human skin.

EXAMPLE 2

360 ml of glycerin (12.2 oz), 719 ml of SURFAX 90 ® (24.2 oz , 360 ml of Tea Tree Blend (12.2 oz) and 719 ml of GERMABEN ® (24.2 oz) were combined and mixed thoroughly. 719g of KELTROL ® (1.6 lbs) was gradually added with stirring. The resulting liquid mixture was added to 19.3 gallons of water and mixed thoroughly for about 15 minutes.

The product has a specific gravity of 0.968, a pH of 6.4 and remained a gel at temperatures of greater than about 110° F. The product had a viscosity as measured using a Brookfield #3 spindle at 20 rpm of 2250 cps. The product tested positive for a surfactant, xanthan gum, GERMABEN II ®, glycerin, Tea Tree Blend and KELTROL ® even after 5 freeze, thaw cycles. No colonies were observed using a microbiological Millipore test.

EXAMPLE 3

A product was prepared as described in Example 2 except that 719g of KELSET ® was substituted for the KELTROL ®.

The product has a specific gravity of 0.99, a pH of 6.7 and remained a gel at temperatures of greater than about 110° F. The product had a viscosity as measured using a Brookfield #3 spindle at 20 rpm of 2500 cps. The product tested positive for a surfactant, xanthan gum, GERMABEN II ®, glycerin, Tea Tree Blend and KELTROL ® even after 5 freeze, thaw cycles. No colonies were observed using a microbiological Millipore test.

In general, the product conforms to the following description:

| | |
|---|---|
| Appearance | A fluid but viscous off-white gel, having a characteristic order. |
| pH | 4.5-7.0 |
| Specific gravity 25° C./25° C. | 0.97-1.02 |
| Viscosity (cps) Brookfield Model RVT, Spindle size #3, Speed 20 rpm | 1000-12000 |
| Total parabens | Between about 0.315 and 0.385% |
| Diazolidinyl Urea (5) | Between about 0.27 and 0.33% |
| Microbiological limits test | Less than 100 Bacteria and less than 100 Molds per ml of product |
| Stability | Over a wide temperature range. |

The product of the invention can be provided either as a gel in the form in which it is made or saturated in a pad or blanket. The pad or blanket is preferably 100% wool and can be of a size large enough to wrap an entire person's body or small enough to cover a small burned portion.

Alternatively, the product can be provided using cotton gauze or any man-made or synthetic bandage carrier. Although woven and nonwoven natural fibrous materials are preferred, the invention is not limited to use with such materials. In a further embodiment, the gel product of the invention can be provided in spray form with an aerosol or equivalent pump-type mechanism.

The product is used by direct application to a burn wound. When the product is provided with a carrier, the entire carrier can be used to cover the burn. Alternatively, the product can be sprayed or otherwise applied directly to the wound site. Debridement of the wound prior to use of the product of the invention is not necessary as the inventive product will actually aid in such debridement.

The burn treatment product of the invention rapidly penetrates through clothing and wets, cools and soothes a burn area. The burn area is wet, cooled and soothed not only on the surface, but also beneath the surface, thereby reducing progression of the area and the severity of the burn. The burn treatment product cools by heat transference and helps to create an isothermic environment when severe and/or massive burns are involved. In addition, the burn treatment product helps reduce the possibility of contamination by completely covering the burn wound and by blocking out air-born bacteria. Clothing and skin tissue do not adhere to the burn treatment product and when the product is removed, no additional pain or skin damage is caused.

The burn treatment product provided in accordance with the invention is non-toxic, bio-degradable, water-soluble and retains its properties even after extended storage. It is suitable for use with any type of burn, including chemical burns. Furthermore, the method of using the product is easy and painless.

It will thus be seen that the objects set forth above, among those made apparent from the preceding description, are efficiently attained and, since certain changes may be made in the above composition of matter without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A burn treatment product in the form of a gel comprising:
   an effective amount of water for permitting formation of a gel and for reducing the amount of heat in the burned area;
   between about 0.1 and 20% Tea Tree Blend; and
   a gel forming amount of at least one gum.

2. The burn treatment product of claim 1, wherein the water is selected from the group consisting of purified water, sterile water, halogenated water and mixtures thereof.

3. The burn treatment product of claim 2, wherein the halogenated water is chlorinated water.

4. The burn treatment product of claim 1, wherein the water is used in an amount between about 80 and 98% by weight of the product.

5. The burn treatment product of claim 4., wherein the water is used in an amount between about 90 and 97% by weight of the product.

6. The burn treatment product of claim 1, wherein the Blend is used in an amount of less than about 20% by weight of the product.

7. The burn treatment product of claim 6, wherein the Blend is used in an amount between about 0.1 and 5.0% by weight of the product.

8. The burn treatment product of claim 7, wherein the Blend is used in an amount between about 0.5 and 1.5% by weight of the product.

9. The burn treatment product of claim 1, wherein the product further comprises tea tree oil.

10. The burn treatment product of claim 9, wherein the total amount of Tea Tree Blend and tea tree oil is less than about 20% by weight of the product.

11. The burn treatment product of claim 10, wherein the total amount of Tea Tree Blend and tea tree oil is between about 0.1 and 5.0% by weight of the product.

12. The burn treatment product of claim 11, wherein the total amount of Tea Tree Blend and tea tree oil is between about 0.5 and 1.5% by weight of the product.

13. The burn treatment product of claim 1, wherein the gum is selected from the group consisting of xanthan gum, locust bean gum, guar gum and mixtures thereof.

14. The burn treatment product of claim 13, wherein the gum is a mixture of xanthan gum and locust bean gum.

15. The burn treatment product of claim 13, wherein the gum is xanthan gum.

16. The burn treatment product of claim 13, wherein the gum is calcium alginate.

17. The burn treatment product of claim 14, wherein the mixture is a 50—50 mixture.

18. The burn treatment product of claim 13, wherein the amount of gum is between about 0.5 and 5.0% by weight of the product.

19. The burn treatment product of claim 18, wherein the gum is used in an amount between about 0.5 and 3% by weight of the product.

20. The burn treatment product of claim 19, wherein the gum is used in an amount between about 0.6 and 1% by weight of the product.

21. The burn treatment product of claim 1, wherein the product further comprises glycerin.

22. The burn treatment product of claim 21, wherein the glycerin is used in an amount of less than about 5% by weight of the product.

23. The burn treatment product of claim 22, wherein the glycerin is used in an amount between about 0.5 and 3% by weight of the product.

24. The burn treatment product of claim 23, wherein the glycerin is used in an amount of about 1% by weight of the product.

25. The burn treatment product of claim 1, wherein the product further comprises iodine.

26. The burn treatment product of claim 25, wherein the iodine is used in an amount between 0.1 and 1% by weight of the product.

27. The burn treatment product of claim 26, wherein the iodine is used in an amount between about 0.01 and 0.1% by weight of the product.

28. The burn treatment product of claim 27, wherein the iodine is used in an amount of about 0.02% by weight of the product.

29. The burn treatment product of claim 1, wherein the product further comprises a surfactant.

30. The burn treatment product of claim 29, wherein the surfactant is selected from the group consisting of SURFAX 90 ® and octoxynol 9.

31. The burn treatment product of claim 29, wherein the amount of surfactant is between about 0.07 and 0.25% by weight of the product.

32. The burn treatment product of claim 31, wherein the amount of surfactant is about 0.14% by weight of the product.

33. The burn treatment product of claim 1, wherein the product further comprises at least one preservative.

34. The burn treatment product of claim 33, wherein the preservative is PHENONIP ®.

35. The burn treatment product of claim 33, wherein the preservative is selected from the group consisting of phenoxy ethanol, methylparaben, ethylparaben, propylparaben, butylparaben and mixtures thereof.

36. The burn treatment product of claim 33, wherein the preservative is used in an amount between about 0.125 and 0.35% by weight of the product.

37. The burn treatment product of claim 36, wherein the preservative is used in an amount between about 0.2 and 0.25% by weight of the product.

38. The burn treatment product of claim 1, wherein the product further comprises methylparaben.

39. The burn treatment product of claim 38, wherein the methylparaben is used in an amount between about 0.01 and 0.5% by weight of the product.

40. The burn treatment product of claim 39, wherein the methylparaben is used in an amount of about 0.25% by weight of the product.

41. The burn treatment product of claim 33, wherein the at least one preservative is imidazolidinyl urea II.

42. The burn treatment product of claim 41, wherein the imidazolidinyl urea II is used in an amount between about 0.1 and 0.35% by weight of the product.

43. A method for treating a burn wound comprising applying a burn treatment product containing at least an effective amount of water to reduce heat in the burned area, between about 0.1 and 20% Tea Tree Blend and a gel forming amount of at least one gum.

44. The burn treatment product of claim 1 further comprising a pad and wherein the pad is saturated with the gel.

45. The burn treatment product of claim 44, wherein the pad is wool.

46. The burn treatment product of claim 1 further comprising a fibrous material and wherein the fibrous material is saturated with the gel.

47. The burn treatment product of claim 1 further comprising an aerosol container and wherein the gel is provided inside the aerosol container and is adapted to be dispensed therefrom in the form of a spray.

48. The burn treatment product of claim 1 further comprising a pump-type container and wherein the gel is provided inside the pump-type container and is adapted to be dispensed therefrom in the form of a spray.

* * * * *